(12) United States Patent
Matera

(10) Patent No.: US 7,810,174 B2
(45) Date of Patent: Oct. 12, 2010

(54) GOGGLE LENS INTERCHANGE SYSTEM

(75) Inventor: Pasquale Matera, Plainview, NY (US)

(73) Assignee: Pasquale Matera, Plainview, NY (US)

( * ) Notice: Subject to any disclaimer, the term of this patent is extended or adjusted under 35 U.S.C. 154(b) by 31 days.

(21) Appl. No.: 11/214,013

(22) Filed: Aug. 30, 2005

(65) Prior Publication Data
US 2006/0191062 A1 Aug. 31, 2006

Related U.S. Application Data

(60) Provisional application No. 60/605,137, filed on Aug. 30, 2004.

(51) Int. Cl.
*A61F 9/02* (2006.01)
(52) U.S. Cl. ............................................ 2/441; 351/86
(58) Field of Classification Search ................ 2/441, 2/426, 428, 430, 436; 351/92, 86, 90, 43
See application file for complete search history.

(56) References Cited

U.S. PATENT DOCUMENTS

| | | | | |
|---|---|---|---|---|
| 4,689,838 A * | 9/1987 | Angermann et al. | ............ | 2/441 |
| 5,523,805 A * | 6/1996 | Kuipers et al. | ................. | 351/86 |
| 5,564,132 A * | 10/1996 | Kuo | ................................ | 2/430 |
| 5,617,588 A * | 4/1997 | Canavan et al. | ................. | 2/428 |
| 5,682,621 A * | 11/1997 | Park | ................................ | 2/441 |
| 5,815,235 A * | 9/1998 | Runckel | ....................... | 351/92 |
| 6,023,791 A * | 2/2000 | Chiang | ........................... | 2/441 |
| 6,349,420 B1 * | 2/2002 | Chiang | ........................... | 2/428 |
| 6,641,263 B2 * | 11/2003 | Olney | ........................... | 351/62 |
| 6,712,465 B1 * | 3/2004 | Teng | ............................ | 351/47 |
| 6,789,273 B2 * | 9/2004 | Markovitz | ...................... | 2/436 |
| 6,863,395 B1 * | 3/2005 | Teng | ........................... | 351/103 |
| 6,923,537 B2 * | 8/2005 | Hartley et al. | .................. | 351/83 |
| 6,964,067 B1 * | 11/2005 | Hartman | ......................... | 2/431 |
| 2009/0019620 A1 | 1/2009 | Reed | | |

* cited by examiner

*Primary Examiner*—Katherine Moran
(74) *Attorney, Agent, or Firm*—Kenealy Vaidya LLP

(57) ABSTRACT

In a goggle lens interchange system, a goggle frame has a ledge on which a lens is removably placed, wherein the ledge is able to be exposed so that a lens of the goggles is able to be removed from the ledge, and another or replacement lens is able to be placed on the ledge.

12 Claims, 18 Drawing Sheets

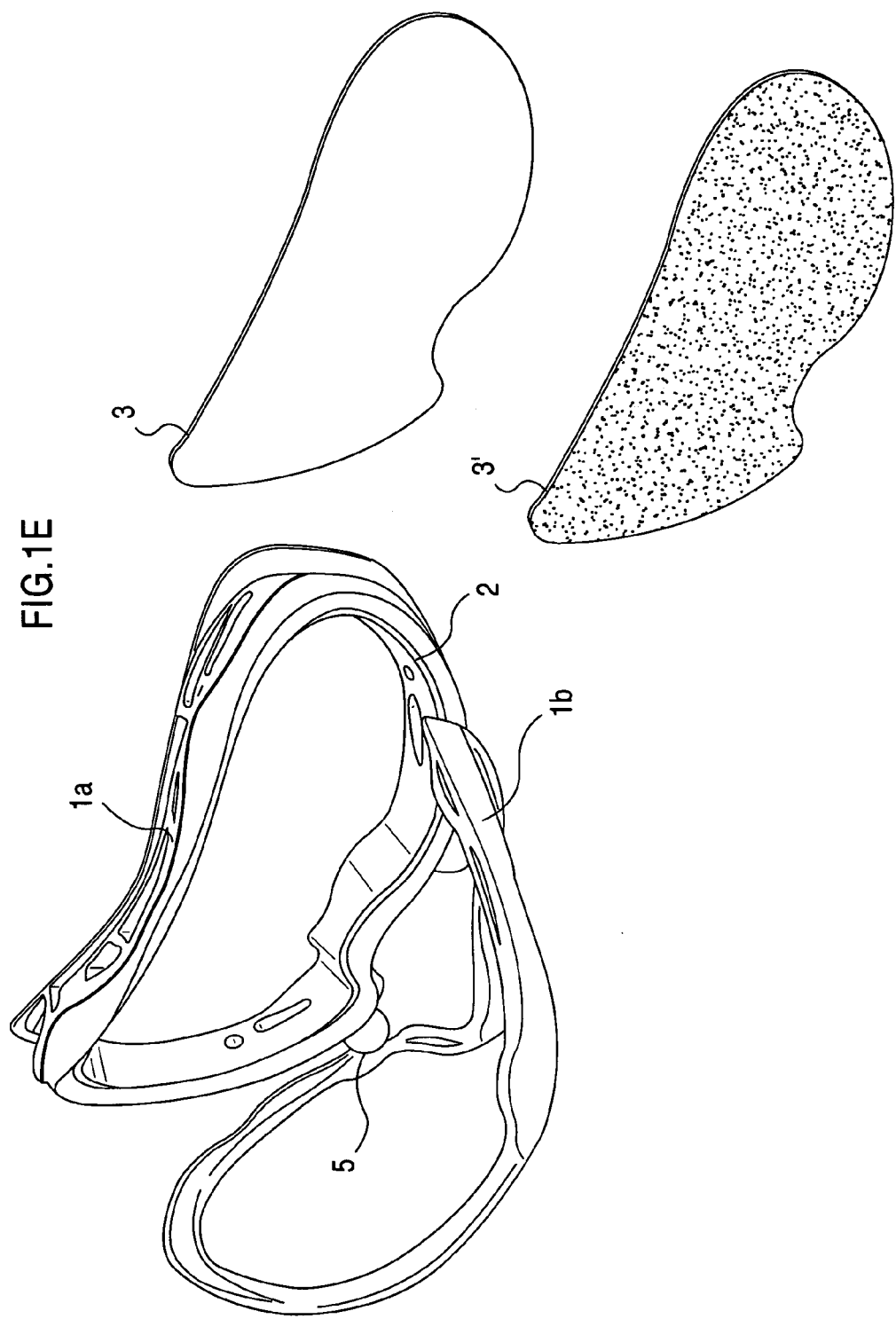

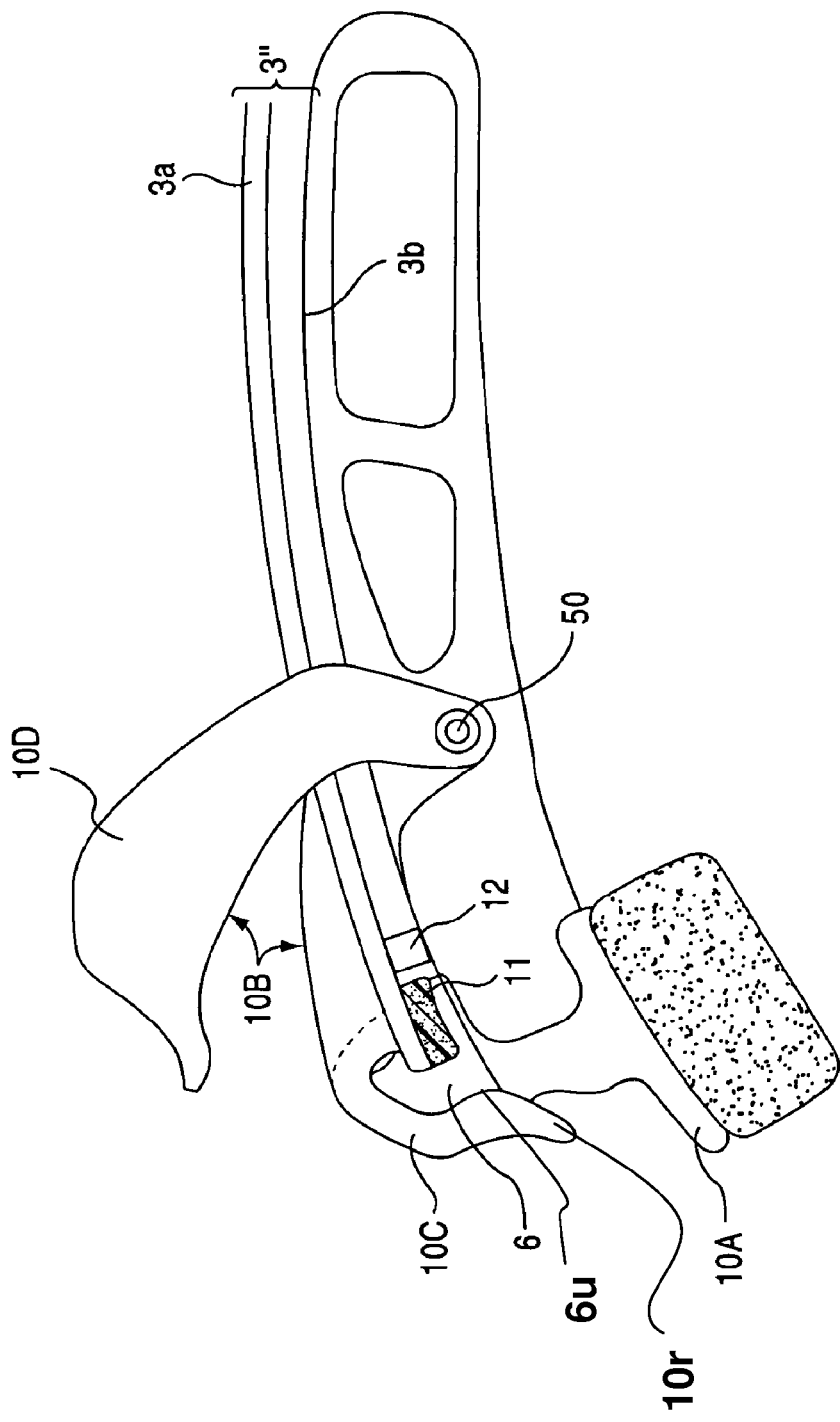

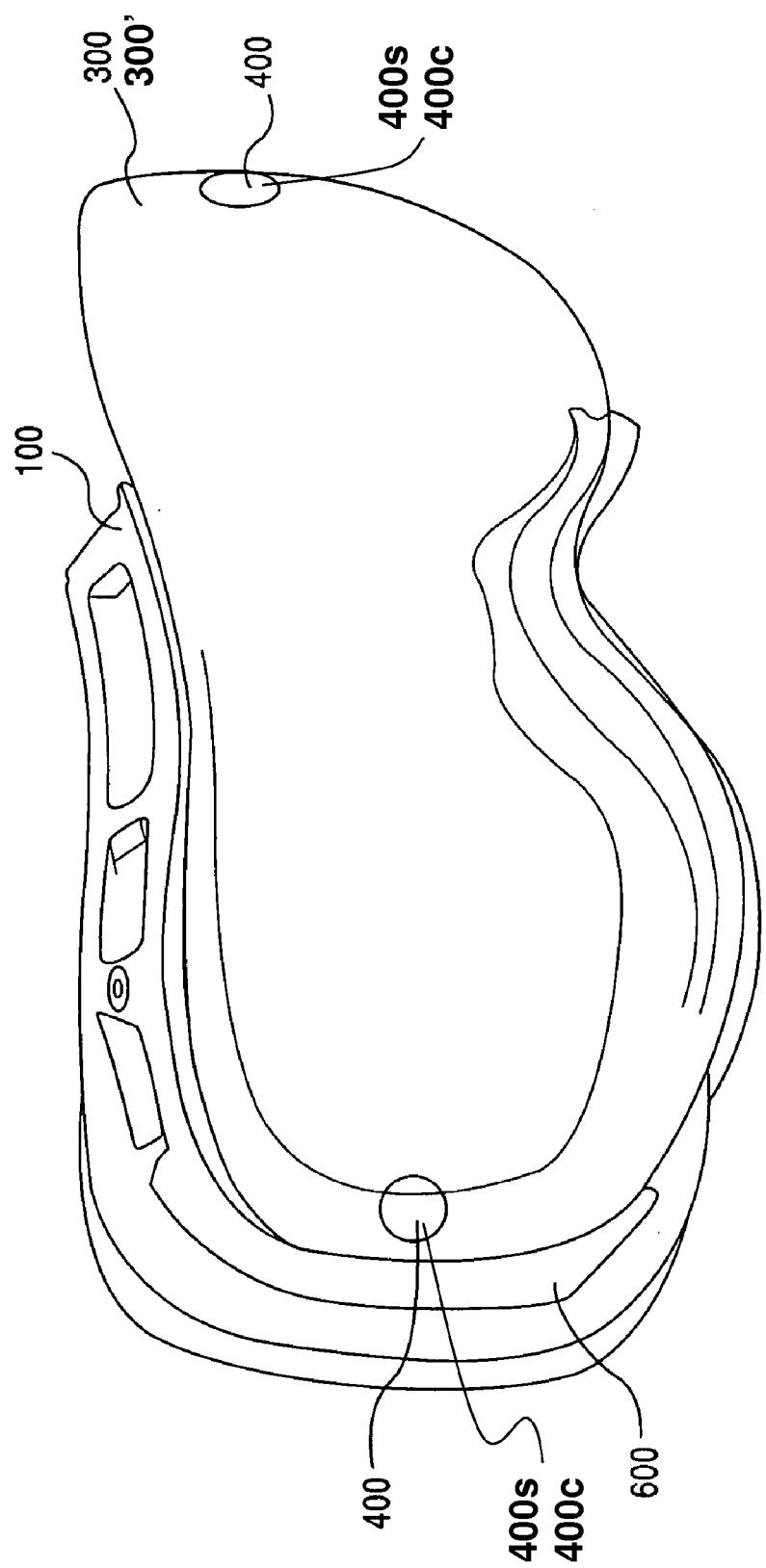

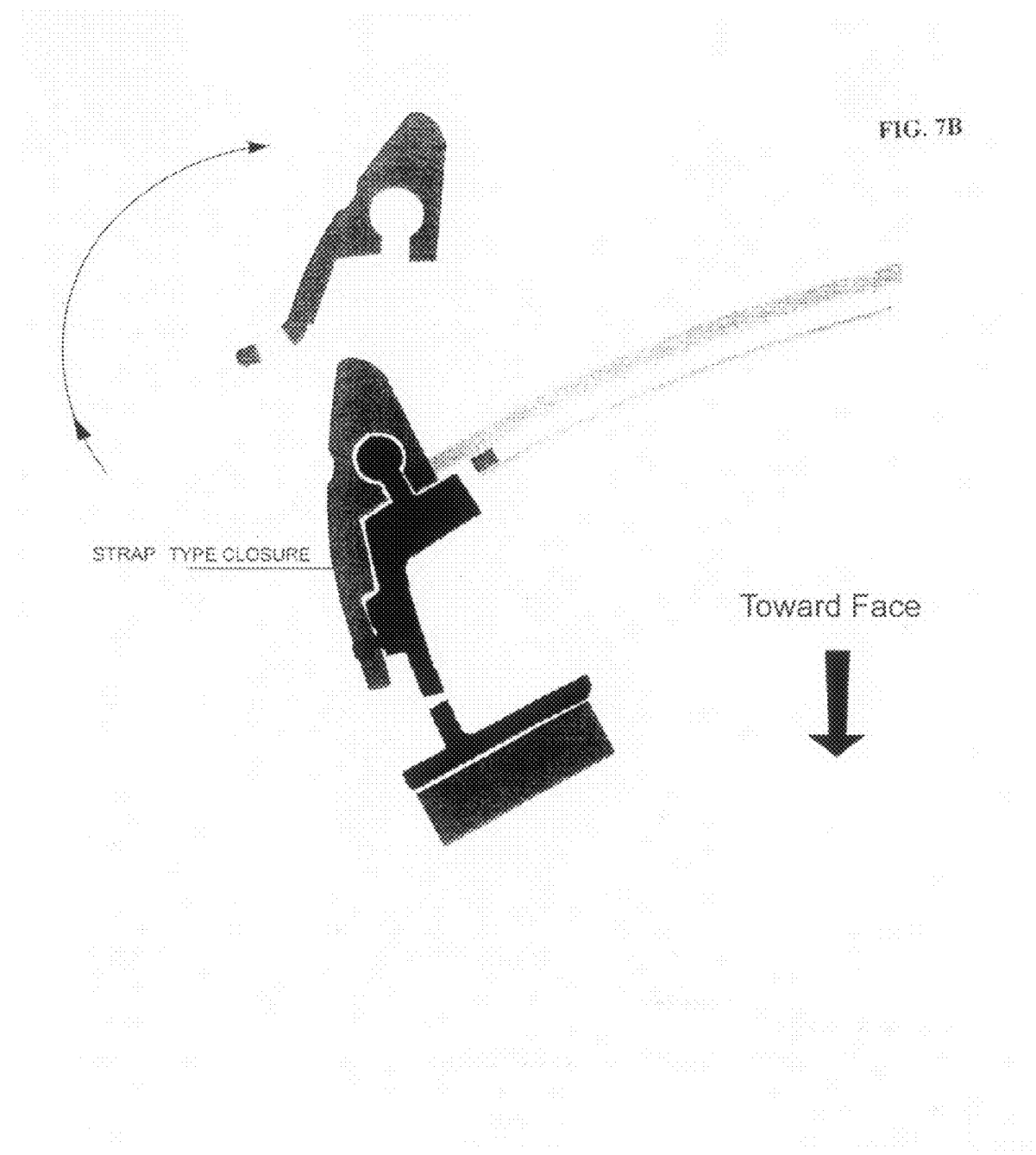

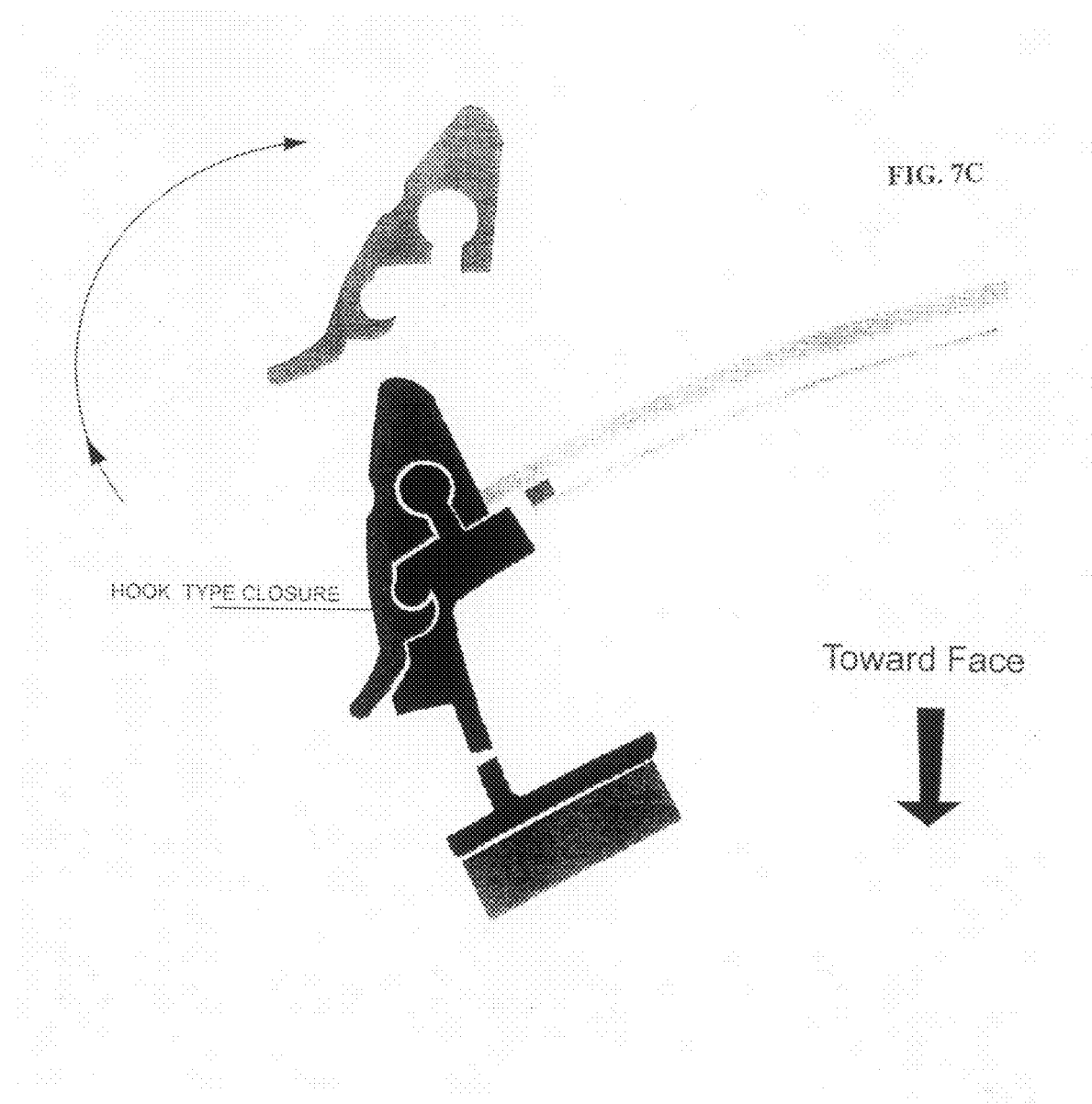

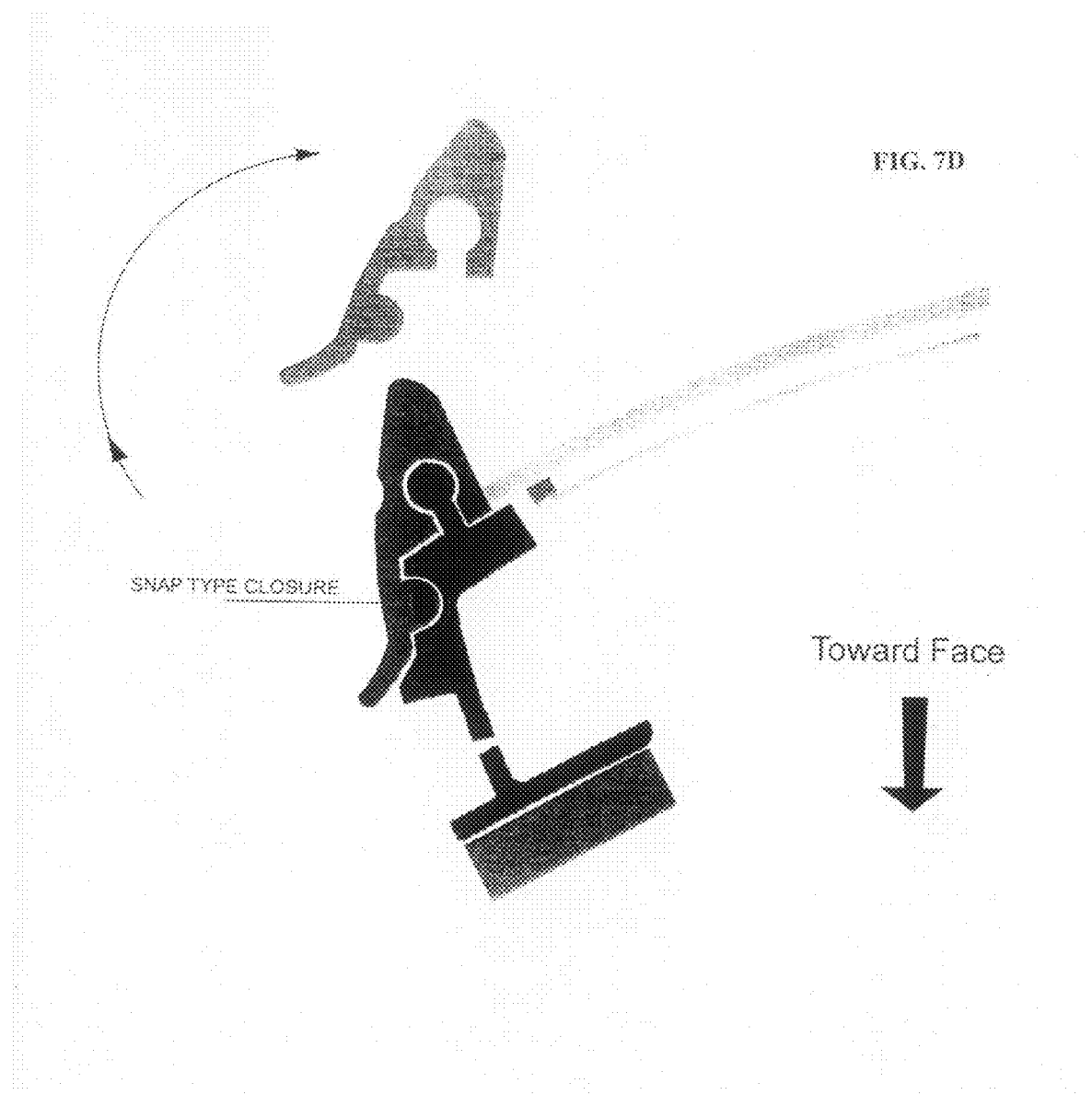

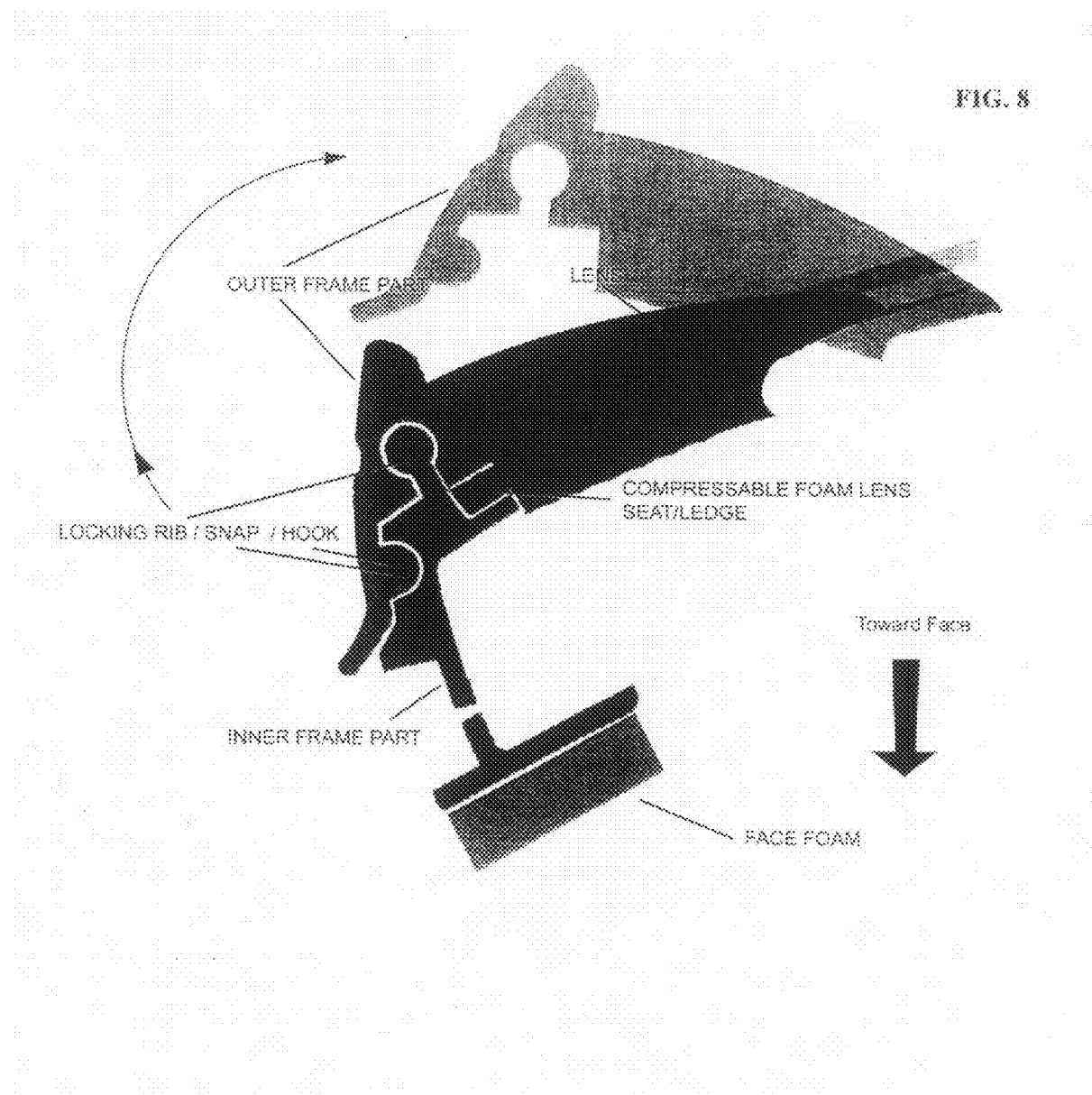

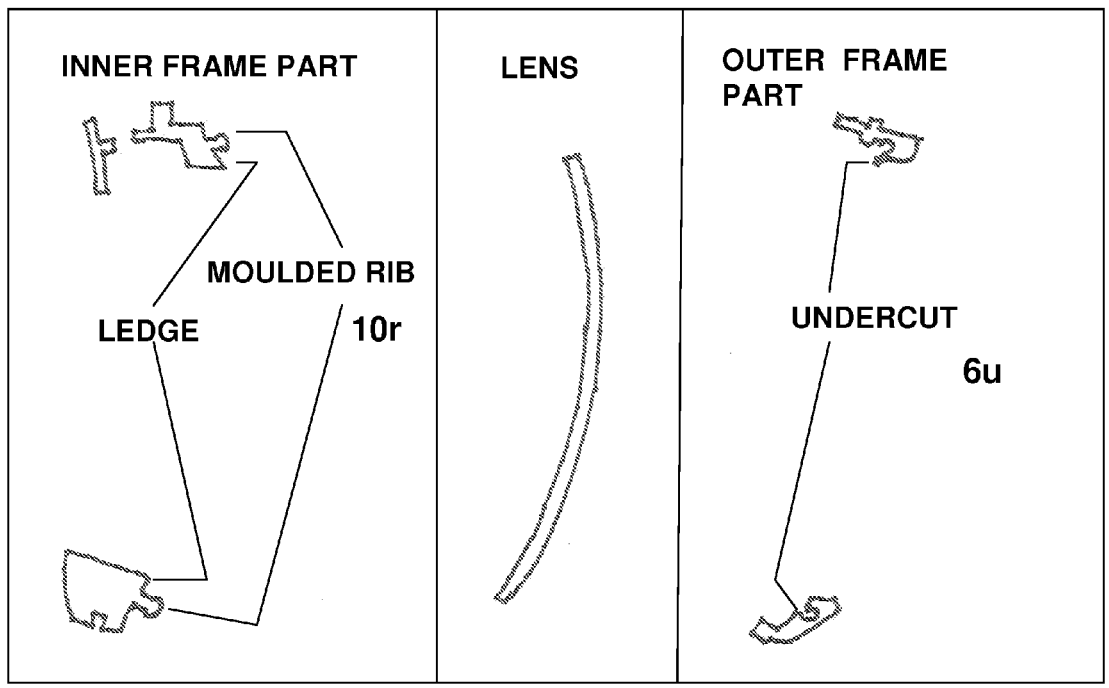
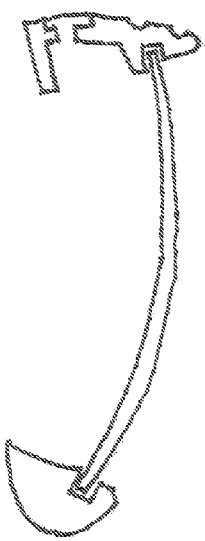
FIG. 9

FIG. 10
INNER FRAME PART
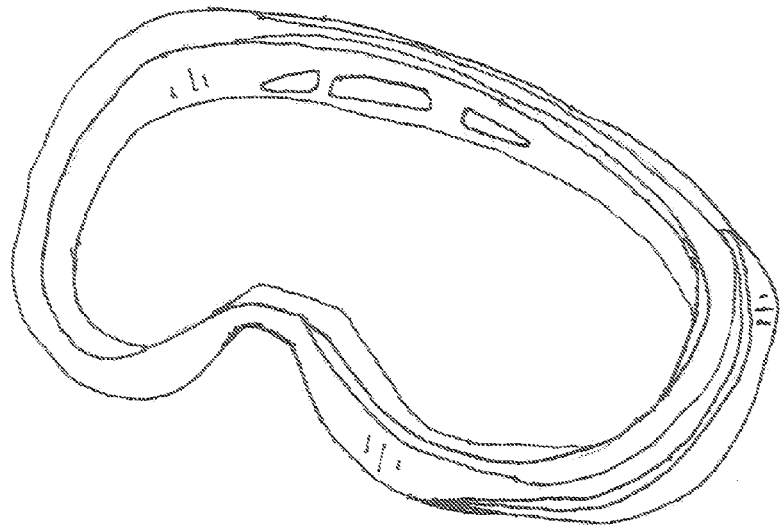
MOULDED RIB 10r
(YELLOW)    LEDGE (RED)
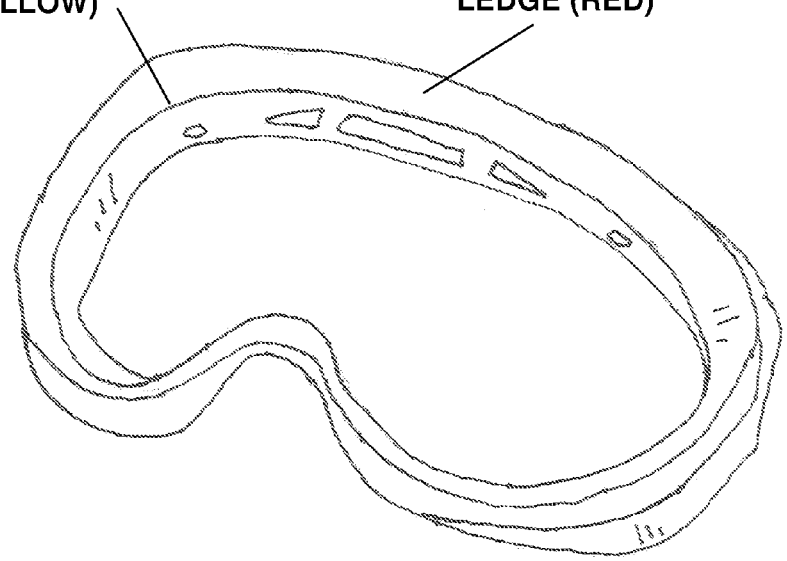

GOGGLE LENS INTERCHANGE SYSTEM

CROSS-REFERENCE TO RELATED APPLICATIONS

This application claims priority of U.S. Provisional Patent Application No. 60/605,137 filed Aug. 30, 2004, the contents of which are hereby incorporated by reference herein.

BACKGROUND OF THE INVENTION

1. Field of the Invention

The present invention is directed to a goggle lens interchange system. More particularly, the present invention is directed to a goggle lens interchange system by which a lens of goggles may be easily removed and replaced, and a method of accomplishing the same.

2. Description of the Related Art

Currently, there are goggles on the market that offer replacement lenses for various light conditions. In such goggles, lenses are removed by sliding them out through a thin slot in the frame and replaced by sliding another or replacement lens into the thin slot in the frame. However, successfully inserting the lens into the thin slot is a difficult, precise, and time-consuming task, which cannot be successfully undertaken under adverse conditions, such as in cold weather, rain, ice, snow, in the dark, or when a user is wearing gloves, such as when skiing. Thus, up until now, goggles promoted as having interchangeable lenses have not been practical for use in the field, e.g., in cold or wet weather, or when a user is wearing gloves, such as when skiing. Therefore, there is a need for goggles that offer a user the ability to quickly and easily change lenses as needed under less than ideal conditions.

SUMMARY OF THE INVENTION

The present invention is therefore directed to a goggle lens interchange system, which substantially overcomes one or more of the problems due to the limitations and disadvantages of the related art.

These and other features and aspects of the present invention may be realized by providing a goggle lens interchange system, including a goggle frame having a ledge on which a lens is removably placed, wherein the ledge is able to be exposed to allow quick and easy lens changes.

These and other features and aspects of the present invention may be realized by providing a method for interchanging a goggle lens, including providing a goggle frame having a ledge for removable seating a lens thereon, exposing the ledge, removing the lens, and placing another or replacement lens on the ledge.

It is therefore a feature of an embodiment of the present invention to provide a goggle lens interchange system, including a goggle frame having a ledge for removably seating a lens thereon, wherein the goggle frame opens to expose the ledge. Preferably, the goggle frame closes to secure the lens on the ledge.

It is therefore a feature of an embodiment of the present invention to provide a goggle lens interchange system, including a rear goggle frame, a front goggle frame, and a ledge for removably seating a lens thereon, wherein the front and rear goggle frames are able to be disengaged on at least three sides thereof to expose the ledge. Preferably, the front and rear goggle frames are able to be engaged to secure the lens on the ledge.

The front and rear goggle frames may be attached by at least one hinging mechanism.

Preferably, the at least one hinging mechanism allows the front and rear goggle frames to be disengaged on at least three sides thereof to expose the ledge.

The ledge may be provided in one of the front goggle frame, the rear goggle frame, or the front and rear goggle frames.

The front goggle frame may be formed of at least two parts. The at least two parts of the front goggle frame may be separately movable to expose the ledge. The at least two parts may include a right part and a left part, a top part and a bottom part, or a combination thereof.

It is another feature of an embodiment of the present invention to provide a goggle lens interchange system, including a rear goggle frame, at least one latch for removably securing a lens to the rear goggle frame, and at least one hinging mechanism for movably attaching the at least one latch to the rear goggle frame.

The rear goggle frame is preferably provided with a ledge for seating a lens thereon.

It is another feature of an embodiment of the present invention to provide a goggle lens interchange system including a rear goggle frame and a plurality of lenses, wherein each of the plurality of lenses is provided with a fastening mechanism for removably attaching one of the plurality of lenses to the rear goggle frame.

The fastening mechanism may be one selected from a hook, a snap, a suction mechanism, and a combination thereof.

It is another feature of an embodiment of the present invention to provide a goggle lens interchange system, including a goggle frame having a front portion and a rear portion, a plurality of lenses, and a ledge provided in one of the front portion of the goggle frame, the rear portion of the goggle frame, or both the front and rear portions of the goggle frame. The plurality of lenses are removably placed onto the ledge. The front portion of the goggle frame and the rear portion of the goggle frame are able to be disengaged on at least three sides thereof to expose the ledge. Preferably, the front portion of the goggle frame and the rear portion of the goggle frame are able to engage each other to secure the lens therebetween.

The front portion of the goggle frame may be formed of at least two parts. The at least two parts of the front portion of the goggle frame may be separately movable to expose the ledge. Preferably, the at least two parts of the front portion of the goggle frame are able to secure the lens between the at least two parts of the front portion of the goggle frame and the rear portion of the goggle frame.

The at least two parts may include a right part and a left part, a top part and a bottom part, or a combination thereof.

The front portion or part(s) of the front portion and rear portion of the goggle frame may be locked together by a snap lock to removably secure the lens therebetween. The snap lock may include a molded rib and undercuts. The molded rib may be provided on the front portion or part(s) of the front portion of the goggle frame and the undercuts may be provided on the rear portion of the goggle frame. Alternatively, the rear portion of the frame may be provided with the molded rib and the front portion or part(s) of the front portion may be provided with the undercuts. In this case, at least the molded rib and undercuts may be formed from semi-rigid molding material.

It is another feature of an embodiment of the present invention to provide a goggle lens interchange system, including a rear goggle frame having a molded lens groove provided on top of foam and/or a compressible gasket, a lens which sits on the molded lens groove, a front goggle frame, and a locking mechanism, wherein the lens is removably secured between the front and rear goggle frames by the locking mechanism, and wherein the front and rear goggle frames may be easily separated to allow access to the lens groove.

A frame of the goggles may be provided with small undercuts around a perimeter thereof to allow the lens to be held lightly in place and self aligned on the ledge until the front portion or part(s) of the front portion is closed.

The lens may include an outer lens separated from an inner lens by at least a gasket. In addition, there may be an air space between the outer and inner lenses.

It is another feature of an embodiment of the present invention to provide a method for interchanging a goggle lens, including providing a goggle frame having a ledge for seating a lens thereon, opening the goggle frame to expose the ledge, removing the existing lens, placing another or replacement lens on the ledge, and closing the goggle frame. Preferably, opening the goggle frame exposes the ledge fully.

It is another feature of an embodiment of the present invention to provide a method for interchanging a goggle lens, including providing a goggle frame having a latch for securing a lens to the goggle frame, opening the latch, removing the existing lens, inserting another or replacement lens, and closing the latch.

It is another feature of an embodiment of the present invention to provide a method for interchanging a goggle lens, including providing a rear goggle frame having a ledge for seating a lens thereon, providing the rear goggle frame with at least one latch and at least one hinging mechanism, wherein the at least one latch is attached to the rear goggle frame by the at least one hinging mechanism, and wherein the at least one latch secures a lens seated on the ledge to the rear goggle frame, swinging the at least one latch on the at least one hinging mechanism in a first direction to allow access to the lens, removing the lens from the ledge, placing another or replacement lens on the ledge, and swinging the at least one latch on the at least one hinging mechanism in a second direction to secure the lens to the rear goggle frame.

It is another feature of an embodiment of the present invention to provide a method for interchanging a goggle lens, including providing a goggle frame and a plurality of lenses each provided with a means for fastening the respective lens to the goggle frame, unfastening one of the plurality of lenses from the goggle frame, and fastening another or replacement lens to the goggle frame.

It is also within the scope of the invention to provide the front goggle frame with one or more latches.

BRIEF DESCRIPTION OF THE DRAWINGS

The above and other features and advantages of the present invention will become more apparent to those of ordinary skill in the art by describing in detail exemplary embodiments thereof with reference to the attached drawings in which:

FIGS. 1C-1F illustrate a method of operating the goggle lens interchange system of FIGS. 1A and 1B;

FIG. 4A illustrates a detailed perspective view of a goggle lens interchange system according to a third embodiment of the present invention.

FIG. 6 illustrates a perspective view of a goggle lens interchange system according to a fourth embodiment of the present invention.

FIGS. 7A-7D illustrate a perspective view of the locking mechanism of a goggle lens interchange system according to an embodiment of the present invention;

FIG. 8 illustrates a perspective view of a goggle lens interchange system according to an embodiment of the present invention;

FIG. 9 illustrates a perspective view of a goggle lens interchange system according to an embodiment of the present invention; and FIG. 10 illustrates a perspective view of a goggle lens interchange system according to an embodiment of the present invention.

DETAILED DESCRIPTION OF THE INVENTION

Figure 1A:
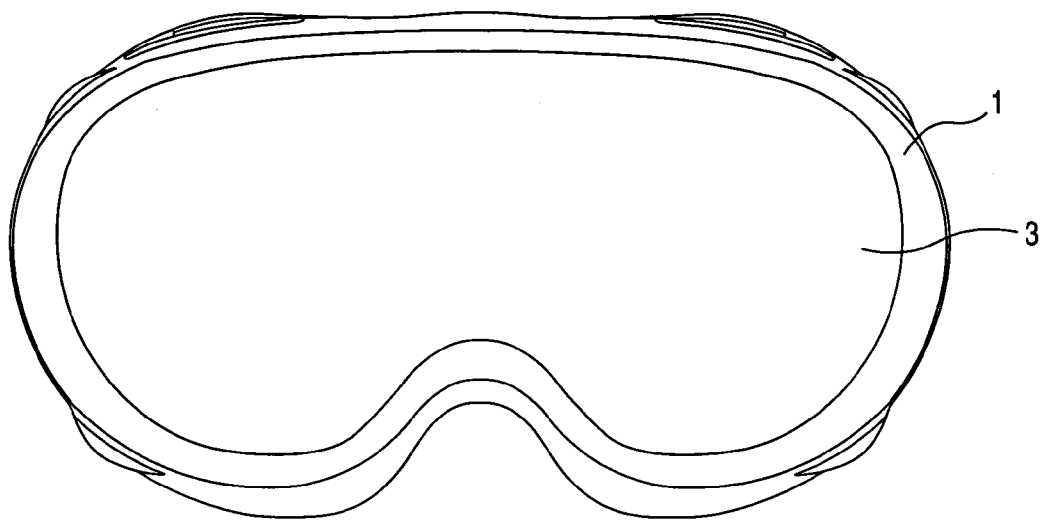
FIGS. 1A and 1B illustrate perspective views of a goggle lens interchange system according to a first embodiment of the present invention.

The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. In the figures, the dimensions of layers and regions may be exaggerated for clarity of illustration. Like reference characters refer to like elements throughout.

Figure 1B:
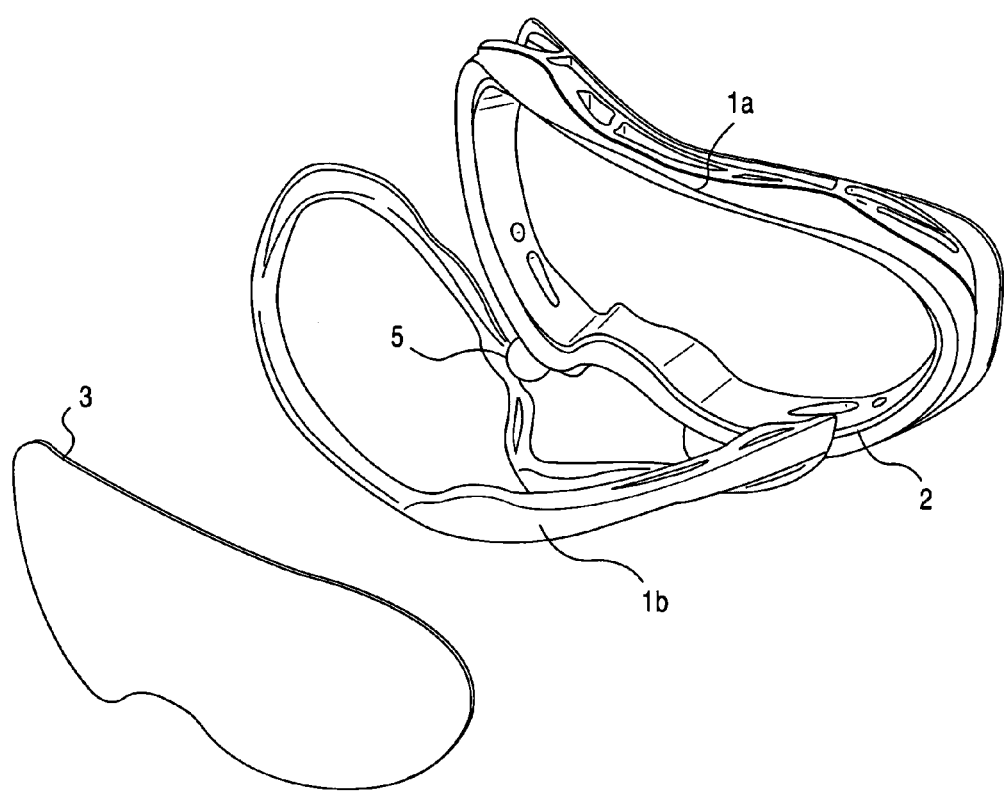

FIGS. 1A and 1B illustrate a goggle lens interchange system according to a first embodiment of the present invention.

As shown in FIGS. 1A and 1B, the goggle lens interchange system of the first embodiment of the present invention includes a frame 1 having a ledge 2 onto which a lens 3 is removably placed. The frame 1 opens, as shown in FIG. 1B, providing a rear portion 1a and a front portion 1b connected by a hinging mechanism 5. The hinging mechanism 5 allows the front and rear frame portions 1b, 1a to be disengaged on at least three sides thereof to allow access to the ledge 2 for easy lens replacement.

The lens of the first embodiment may include an outer lens separated from an inner lens by at least a gasket. In addition, there may be an air space between the outer and inner lenses. An example of such a lens is illustrated in FIG. 4A.

An exemplary method of operating the goggle lens interchange system of FIGS. 1A and 1B will now be described with respect to FIGS. 1C-1F.

Figure 1C:
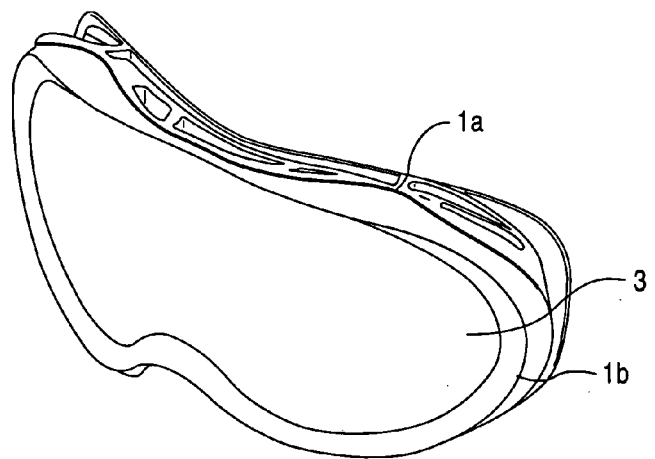

As shown in FIG. 1C, the lens 3 is removably positioned on the ledge 2 (FIG. 1D), and the front and rear frame portions 1b, 1a are closed with the lens 3 sealed therebetween.

Figure 1D:
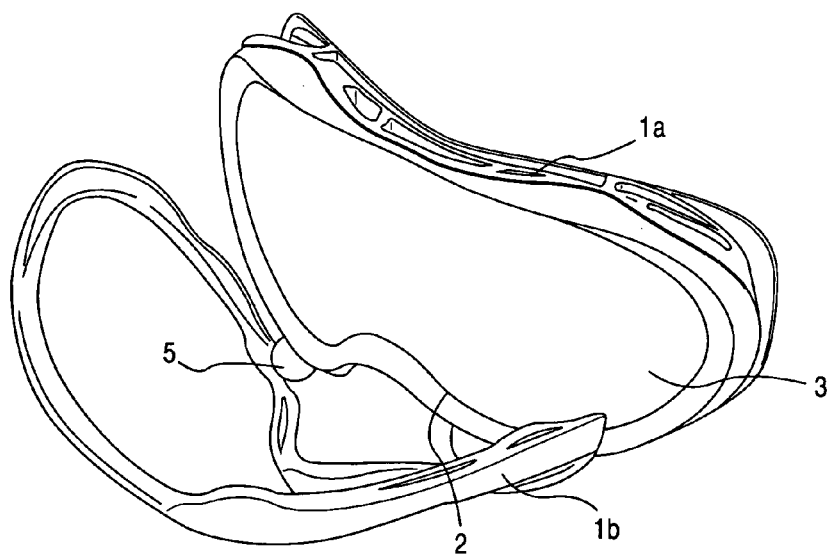

In FIG. 1D, the front frame portion 1b is separated from the rear frame portion 1a on three sides, providing access to the ledge 2. Movement of the front and rear frame portions is enabled by the hinging mechanism 5.

Figure 1F:
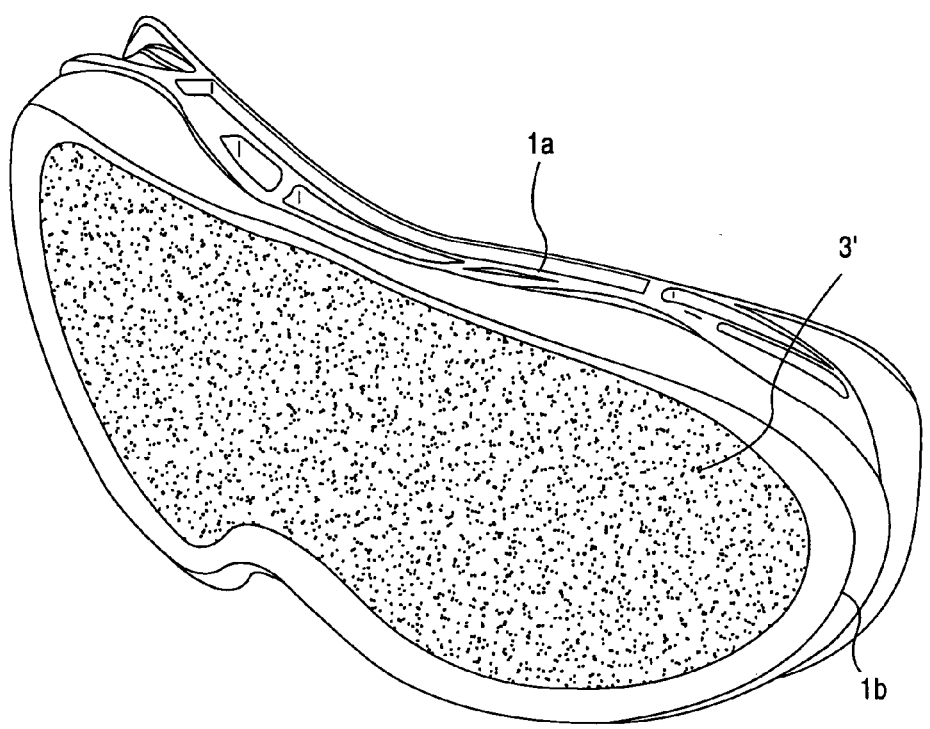

Access to the ledge 2, provided by separating the front and rear frame portions 1b, 1a, allows the lens 3 to be easily removed from the ledge 2, as shown in FIG. 1E. Another or replacement lens 3' may then be positioned on the ledge 2 and the front and rear frame portions 1b, 1a closed, thereby easily providing a goggle having the lens 3' sealed between the front and rear frame portions 1b, 1a, as shown in FIG. 1F.

Thus, by the present invention, a user is able to quickly and easily remove a lens and replace it with a different lens. Therefore, if, for example, a user is skiing and the sun begins to set, he or she may switch to a clear lens right on the lift or mountain, without having to return to the lodge, and without having to remove his or her gloves.

The goggle lens interchange system of the first embodiment may further include a locking mechanism (not shown) for holding the front and rear frame portions 1b, 1a together. The locking mechanism secures the front and rear frame portions 1b, 1a together with the lens 3 therebetween.

In this case, a user may unlock the locking mechanism, open the frame 1 revealing the ledge 2, remove the lens 3, place another or replacement lens such as lens 3' onto the ledge 2, close the frame 1, and re-lock the locking mechanism quickly and easily even in extreme conditions, such as on the top of a snowy mountain, while wearing gloves.

Figure 2:
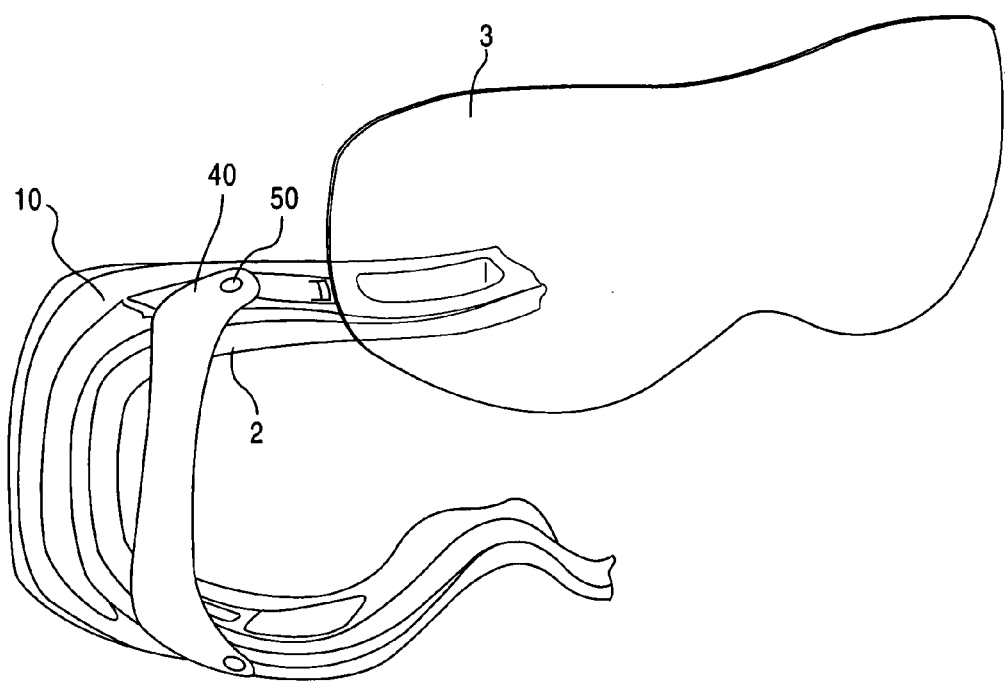
FIG. 2 illustrates a perspective view of a goggle lens interchange system according to a second embodiment of the present invention.

FIG. 2 illustrates a goggle lens interchange system according to a second embodiment of the present invention. As shown in FIG. 2, the goggle lens interchange system of the second embodiment includes a rear goggle frame 10, having a ledge 2 onto which a lens 3 is removably placed, and at least one latch 40 moveably connected to the rear goggle frame 10 by a hinging mechanism 50, for removably securing the lens 3 to the rear goggle frame 10. The latch 40 opens to allow access to the ledge 2 for easy lens changes. Thus, similar to the first embodiment, a user may quickly and easily change lenses even in adverse conditions.

The lens in this embodiment may also include an outer lens separated from an inner lens by at least a gasket. In addition, there may be an air space between the outer and inner lenses. An example of such a lens is illustrated in FIG. 4A.

In FIG. 2, a latch 40, i.e., one, is shown on the right side, from a wearer's perspective, of the goggle frame. However, a position of a latch and/or a hinging mechanism of the present invention is not limited to what is shown in FIG. 2. For example, a similar latch and hinging mechanism may be disposed on the left side (from a wearer's perspective), a top, a bottom or any other portion of the goggle frame. In addition, as previously noted, there may be more than one latch and hinging mechanism, which may be disposed on right and left sides of the goggle frame, on a top and bottom of the goggle frame, or on any other combination of portions of the goggle frame.

Figure 5A:
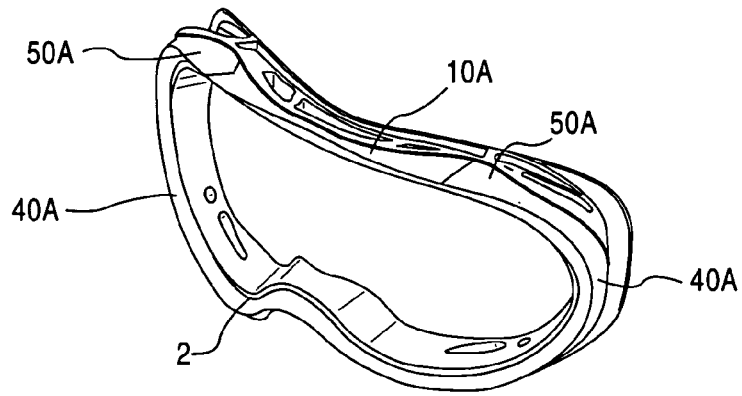
FIGS. 5A-5C illustrate views showing variations of the goggle lens interchange system of FIG. 2.
Figure 5B:
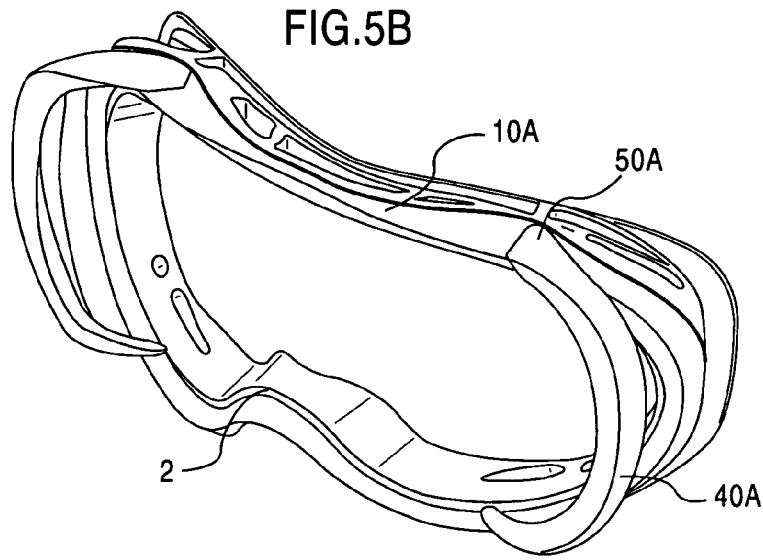

FIGS. 5A and 5B illustrate a case where there are two latches 40A and two hinging mechanisms 50A disposed on right and left sides of a rear goggle frame 10A. The latches 40A open by swinging towards each other in an inward direction, thereby revealing the ledge 2.

Further, the hinging mechanism 50 is not limited to the position thereof illustrated in FIG. 2. That is, a latch may be disposed in the same position as the latch 40 of FIG. 2, but a hinging mechanism may be disposed at a middle portion of the latch, as opposed to being at end portions of the latch, as illustrated in FIG. 2. In such a case, the hinging mechanism would connect the latch to a middle portion, in the vertical direction, of a right side of the goggle frame.

Figure 5C:
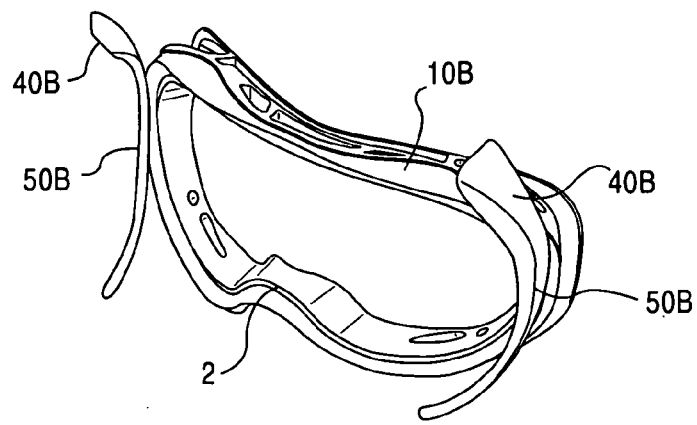
Figure 7A:
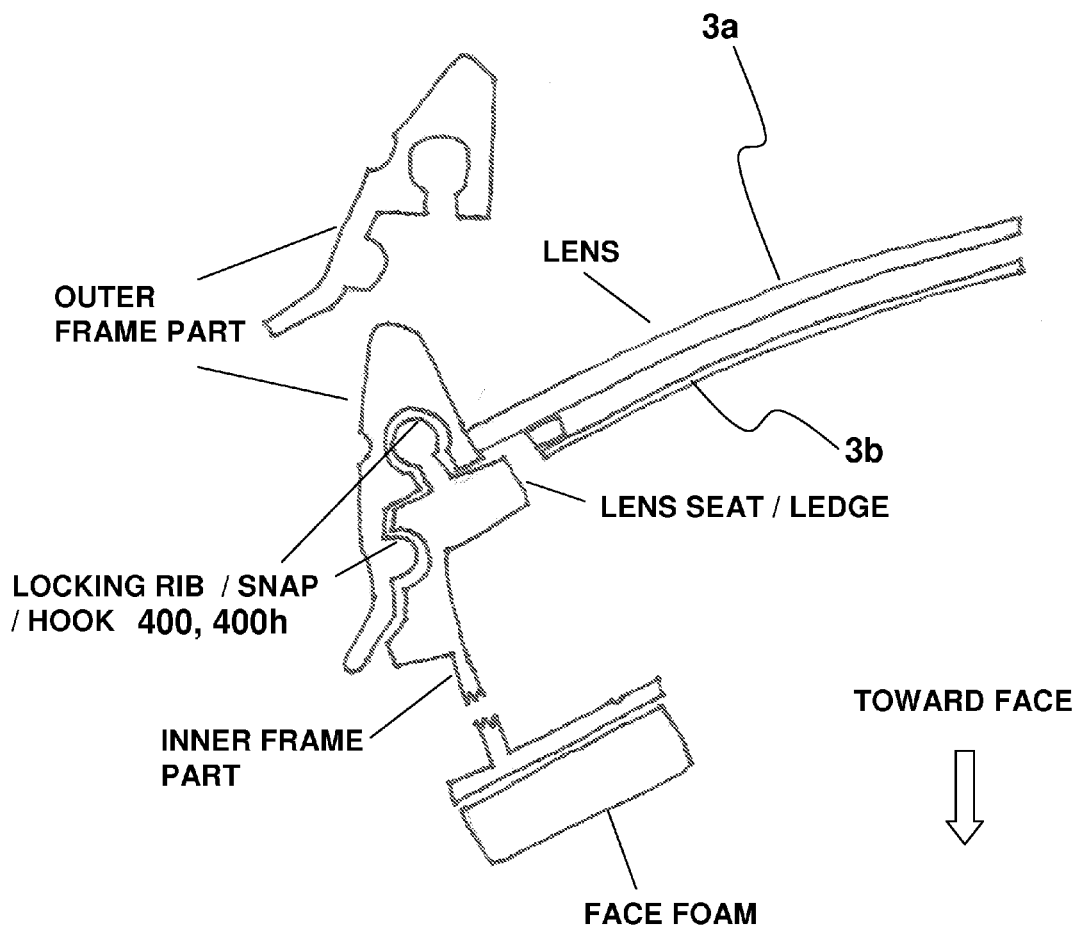

FIG. 5C illustrates a case where there are two latches 40B and two hinging mechanisms 50B disposed at right and left sides of a rear goggle frame 10B. In the variation of the second embodiment shown in FIG. 5C, the hinging mechanisms 50B are positioned at a center, in the vertical direction, of the latches 40B and sides of the rear goggle frame 10B. In this case, the latches 40B open by swinging away from each other in an outward direction, thereby revealing the ledge 2.

In addition, in the present invention, a hinging mechanism may be disposed at any portion or portions of a latch, a pair of latches, or a plurality of latches, regardless of number, or placement, of the latch(es).

The goggle lens interchange system of the second embodiment, and variation thereof, may further include strap holder parts (not shown), which cover the latch or latches. In this case, by wearing the goggles, the latch(es) may be restrained from opening.

FIGS. 3A-3D illustrate a method of operating the goggle lens interchange system of FIG. 2.

Figure 3A:
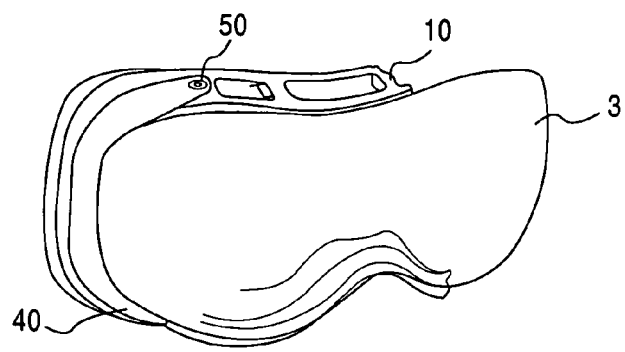
FIGS. 3A-3D illustrate a method of operating the goggle lens interchange system of FIG. 2.

As shown in FIG. 3A, the lens 3 is secured in place against the rear goggle frame 10 by the latch 40, which is attached to the rear goggle frame 10 by the hinging mechanism 50.

Figure 3B:
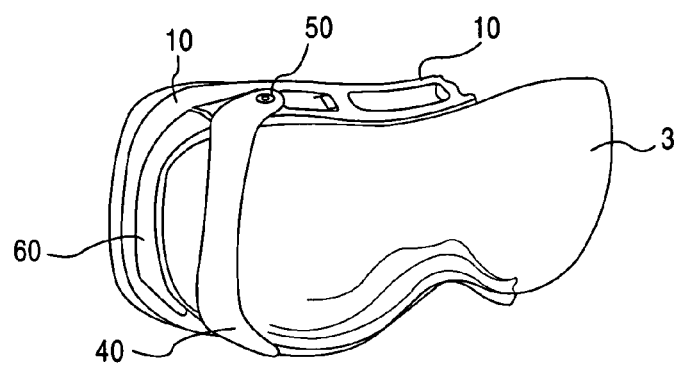

In FIG. 3B, the latch 40 is partially open, movement thereof being enabled by the hinging mechanism 50. Also shown in FIG. 3B is a locking mechanism 60, which may include a snap lock, wherein the latch 40 is provided with an edge that snaps into the locking mechanism 60 to be held securely in place. The edge of the latch 40 and the locking mechanism 60 may be formed of molded plastic or a semi-rigid material that allows the edge of the latch 40 to snap into or under the locking mechanism 60, which may be a groove formed into a side of the rear goggle frame 10.

Figure 3C:
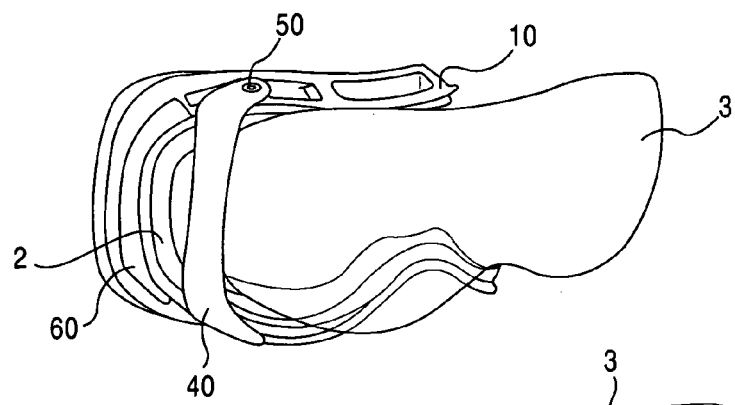

In FIG. 3C, the ledge 2 is accessible by opening the latch 40 via the hinging mechanism 50, wherein the lens 3 is shown partially removed from the ledge 2 of the rear goggle frame 10.

Figure 3D:
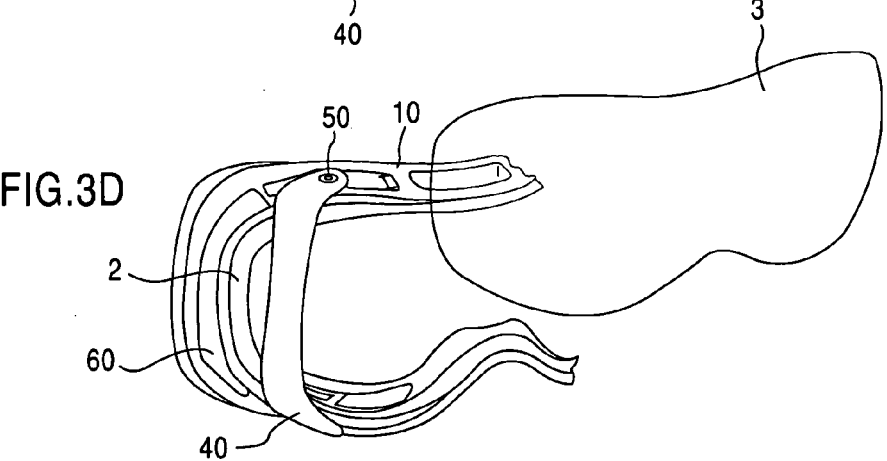

In FIG. 3D, the lens 3 is completely removed from the rear goggle frame 10 and the ledge 2 is completely exposed. Thus, a different or a replacement lens (not shown) may be placed on the ledge 2 and the latch 40 may be closed by being swung on the hinging mechanism 50 and snapped into the locking mechanism 60 by a user. The method above applies equally, with minor variations, to a goggle interchange system of the present invention in which a number and/or placement of latch(es), hinging mechanism(s) and/or locking mechanisms(s) varies from those shown in FIGS. 2 and 3A-3D. For example, the method applies, with minor variations, to the goggle lens interchange system of FIGS. 5A-5C.

FIG. 4A illustrates a top perspective view of a goggle lens interchange system according to a third embodiment of the present invention.

As shown in FIG. 4A, a lens 3', having an outer lens 3a and an inner lens 3b and an air space therebetween, is positioned on a molded ledge 6 of a rear goggle frame 10A, on top of foam 11 and a compressible gasket 12. A front f part of a goggle frame 10B is provided in such a manner as to be able to be in at least an open position, illustrated as 10D, or a closed position, illustrated as 10C. Movement of the front part 10B is provided for by a hinging mechanism 50, which also serves to connect the front part 10B to the rear goggle frame 10A. The front part in the closed position 10C compresses the foam 11 and compressible gasket 12, forming a seal between the lens 3" and the molded ledge 6 of the rear goggle frame 10A. The front part in the closed position 10C may lock the lens 3" in place by a snap, undercut, cam, or any other suitable locking mechanism. For example, the molded ledge 6 may include an undercut portion into which a molded edge of the front part 10B may be snapped when the front part is in the closed position 10C. In this embodiment, the foam 11 and/or compressible gasket 12 may act as a filter/gasket and a spring to allow the front part when closed 10C to cam over the lens 3" and snap closed.

Although the lens 3" illustrated in FIG. 4A includes the outer lens 3a and the inner lens 3b with an air space therebetween, the third embodiment is not limited to such a lens. Any appropriate lens may be used in any of the embodiments of the present invention.

Figure 4B:
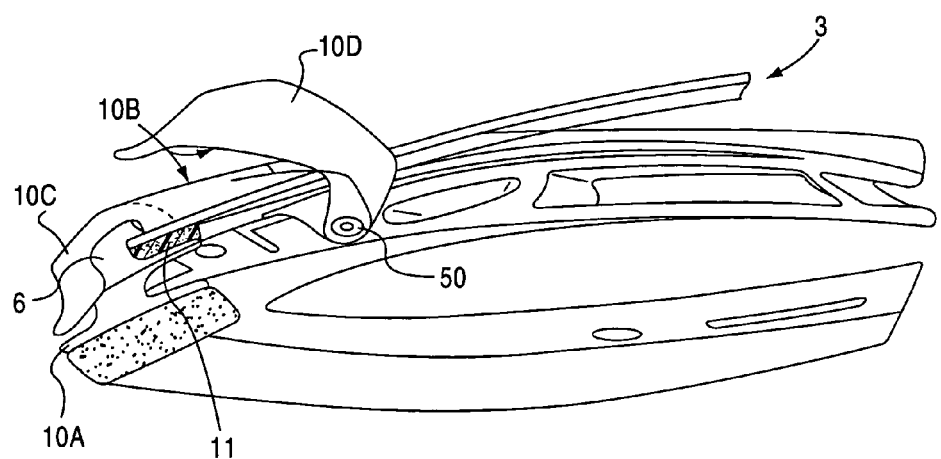
FIG. 4B illustrates a variation thereof.

FIG. 4B illustrates a variation of the third embodiment shown in FIG. 4A, in which the foam acts as a filter, a gasket, and a spring, as described with respect to FIG. 4A.

The goggle lens interchange system of the third embodiment and variants thereof may include more than one front part 10B. In addition, the goggle lens interchange system of the third embodiment may further include strap holder parts (not shown), which cover the front part or parts. In this case, by wearing the goggles, the front part or parts may be restrained from opening. Further, the front part or parts may be formed of a latch or latches, similar to those of the second embodiment, and may operate in a manner similar to that shown in FIGS. 3A-3D, with respect to the second embodiment.

In addition, features of the third embodiment may be included in the first and second embodiments, as well. For example, the ledge of the first and second embodiments may be a molded groove provided on top with foam and/or a compressible gasket. The foam and/or compressible gasket may be compressed between the front and rear frame portions or the rear frame portion and latch(es) to form a seal with the lens therebetween. The foam and/or compressible gasket may act as a filter or gasket, and may also act as a spring to allow the front portion(s) or latch(es) to cam over the lens and snap closed by means of a snap or cam or any other locking mechanism.

For example, the front portion(s) or the latch(es) may be provided with a molded rib 10r and the rear frame portion with an undercut or undercuts 6u to be locked together with a lens therebetween. Alternately, the front portion(s) or latch(es) may be provided with undercuts and the rear frame portion with a molded rib. Such molded rib and undercuts may serve to form a snap lock, whereby the front part(s) or latch(es) and the rear goggle frame may be locked together. The snap lock may work in a manner similar to a ball and socket, or a coffee cup and lid, to removably secure the lens therebetween. At least the molded rib and undercuts may be formed from semi-rigid molding materials that are flexible enough to allow such closures.

Although not shown in the drawings, in the above embodiments, latch(es) or front portion(s) of a goggle frame may be completely removed from the goggle frame or portion thereof by disengaging the hinging mechanism. In addition, a locking mechanism may be a snap, a cam, a latch or any other means by which the front and rear frame portions are locked together.

FIG. 6 illustrates a perspective view of a goggle lens interchange system of a fourth embodiment of the present invention.

As illustrated in FIG. 6, a goggle lens interchange system according to a fourth embodiment of the present invention includes a rear frame portion 100 having a ledge and a lens 300 provided with a mechanism for locking to the rear frame portion 100. The mechanism for locking to the rear frame portion 100 may be snaps (snap locks) 400, hooks 400h, cam 400c, or any other means provided at least in part on the lens 300 whereby the lens 300 may be removably attached to the rear frame 100. Thus, the lens 300 of the goggle may be easily removed and replaced with another or a replacement lens 300'. In this embodiment, a frame or eyewire may be of minimal size, thereby producing a wider field of view for a user. The lens 300 may have a outer lens and an inner lens with an air space therebetween, similar to the lens 3" shown in FIG. 4A.

The goggle lens interchange system of the fourth embodiment may further include a locking mechanism 600 similar to the locking mechanism 60 of FIGS. 3B-3D described with respect to the second embodiment.

FIGS. 7A-7D illustrate a perspective view of the locking mechanism of a goggle lens interchange system according to an embodiment of the present invention;

FIG. 8 illustrates a perspective view of a goggle lens interchange system according to an embodiment of the present invention;

FIG. 9 illustrates a perspective view of a goggle lens interchange system according to an embodiment of the present invention; and FIG. 10 illustrates a perspective view of a goggle lens interchange system according to an embodiment of the present invention.

In the embodiments described above, a lens may be provided with small undercuts around a perimeter thereof to allow the lens to be held lightly in place and self aligned on the ledge or in the molded portion until the front part(s), latch(es), or locking mechanism are closed and/or secured.

In addition, front part(s), latch(es), hinging mechanism(s), locking mechanism(s), and/or other components of the invention described above with respect to various embodiments are not limited to the positions thereof illustrated in the respective drawings. As previously noted, the invention may be embodied in different forms and should not be construed as limited to the embodiments set forth and illustrated herein.

According to the present invention, a ledge component of a goggle on which a lens rests may be exposed, thereby allowing a lens of the goggle to be changed quickly and easily, without the need to align and insert the lens into a narrow groove, which is very difficult and time consuming and nearly impossible in the field and in cold conditions.

By the features of the embodiments of the present invention described above, a goggle lens may be easily and quickly removed and replaced in the field, under adverse conditions, making the concept of interchangeable goggle lenses practical for users.

Exemplary embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A goggle lens interchange system, comprising:
   a rear goggle frame including an inner curved surface configured to face towards a user's face when the user is wearing the goggle lens interchange system and an outer curved surface;
   a lens, the lens having a surface in direct contact with the rear goggle frame;
   a front goggle frame, operationally connected to the rear goggle frame such that the front goggle frame is movable between a first position and a second position, wherein the lens is located between the front goggle frame and the outer curved surface of the rear goggle frame when located in the first position to secure the lens between the front goggle frame and rear goggle frame, and at least a portion of the front goggle frame is spaced from both the outer curved surface of the rear goggle frame and lens when in the second position; and
   at least one hinge mechanism having a rotational axis substantially parallel with a longitudinal axis of at least one of the rear goggle frame and the front goggle frame, the hinge mechanism connected to the rear goggle frame and the front goggle frame, wherein the front goggle frame includes left and right eye portions separated by a concave portion configured to receive a user's nose, the entire front goggle frame is configured to rotate about the at least one hinge mechanism such that the front goggle frame rotates about an axis that is substantially parallel with the longitudinal axis of the front goggle frame.

2. The goggle lens interchange system as claimed in claim 1, further comprising a locking mechanism that separately locks the front goggle frame and the rear goggle frame together to removably secure the lens therebetween.

3. The goggle lens interchange system as claimed in claim 2, wherein the locking mechanism includes a snap lock, the snap lock formed of a molded rib provided on one of the front goggle frame and the rear goggle frame and includes undercuts provided in the other of the front goggle frame and the rear goggle frame, the undercuts and molded rib being formed to allow the undercuts to be snapped into the molded rib.

4. The goggle lens interchange system of claim 2, wherein the locking mechanism is pivotally connected to the goggle frame.

5. The goggle lens interchange system as claimed in claim 1, wherein the at least one hinging mechanism allows the front goggle frame to pivot away from the rear goggle frame on at least three sides thereof.

6. The goggle lens interchange system as claimed in claim 1, further comprising a foam layer and a compressible gasket formed on the rear goggle frame, wherein a seal is formed between the rear goggle frame and the lens by compressing the foam and the compressible gasket therebetween.

7. The goggle lens interchange system of claim 1, wherein the lens has a surface with a perimeter edge having a concave portion separating left and right lens portions.

8. A goggle lens interchange system, comprising:
a goggle frame;
a first locking mechanism and a second locking mechanism, operationally connected to the goggle frame; and
a lens having a surface in direct contact with the goggle frame, wherein the first locking mechanism and the second locking mechanism are configured to secure the lens to the goggle frame and wherein the lens has a surface with a perimeter edge having a concave portion separating left and right lens portions, and the first locking mechanism and the second locking mechanism are located adjacent the left and right lens portions, respectively, such that the concave portion of the lens is located between the first locking mechanism and the second locking mechanism.

9. A method for interchanging lenses in a goggle, the method comprising:
providing a rear goggle frame including an inner curved surface configured to face towards a user's face when the user is wearing the goggle and an outer curved surface;
providing a lens having an inner curved surface configured to face towards a user's face when the user is wearing the goggle, an outer curved surface, and a concave portion configured to receive a user's nose and separating left and right portions of the lens;
providing a front goggle frame operationally connected to the rear goggle frame such that the front goggle frame is movable with respect to the rear goggle frame from a closed position to an opened position;
placing the front goggle frame in the opened position wherein at least a portion of the front goggle frame is spaced from the rear goggle frame;
placing the lens directly on the outer curved surface of the rear goggle frame while the front goggle frame is in the opened position; and
closing the front goggle frame with respect to the rear goggle frame such that the front goggle frame is in the closed position and a portion of the lens is located between the front goggle frame and the rear goggle frame in a manner such that a line normal to the outer curved surface of the portion of the lens located between the front goggle frame and the rear goggle frame intersects both the rear goggle frame and front goggle frame.

10. The method for interchanging lenses in a goggle as claimed in claim 9, further comprising:
providing the rear goggle frame with a latch for securing the lens to the rear goggle frame;
opening the latch and removing the lens;
inserting a replacement lens in the rear goggle frame; and
closing the latch, wherein the replacement lens is securably retained within the rear goggle frame.

11. The method for interchanging lenses in a goggle as claimed in claim 10, further comprising:
providing the rear goggle frame with at least one hinging mechanism, wherein the latch is pivotally attached to the rear goggle frame by the at least one hinging mechanism, and wherein the latch secures the lens seated to the rear goggle frame;
pivoting the latch on the at least one hinging mechanism in a first direction to allow access to the lens; and
pivoting the latch on the at least one hinging mechanism in a second direction to secure the lens to the rear goggle frame.

12. A goggle lens interchange system, comprising:
a rear goggle frame including an inner curved surface configured to face towards a user's face when the user is wearing the goggle lens interchange system and an outer curved surface;
a lens, the lens having a surface in direct contact with the rear goggle frame;
a front goggle frame, operationally connected to the rear goggle frame such that the front goggle frame is movable between a first position and a second position, wherein the lens is located between the front goggle frame and the outer curved surface of the rear goggle frame when located in the first position to secure the lens between the front goggle frame and rear goggle frame, and at least a portion of the front goggle frame is spaced from both the outer curved surface of the rear goggle frame and lens when in the second position;
at least one hinge mechanism having a rotational axis substantially parallel with a longitudinal axis of at least one of the rear goggle frame and the front goggle frame, the hinge mechanism connected to the rear goggle frame and the front goggle frame; and
a locking mechanism that separately locks the front goggle frame and the rear goggle frame together to removably secure the lens therebetween, wherein the locking mechanism is pivotally connected to the goggle frame.

* * * * *